United States Patent [19]

Fujii

[11] Patent Number: 5,285,786

[45] Date of Patent: Feb. 15, 1994

[54] APPARATUS AND METHOD FOR RADIOGRAPHIC DIAGNOSIS

[75] Inventor: Senzo Fujii, Ootawara, Japan

[73] Assignee: Kabushiki Kaisha Toshiba, Kawasaki, Japan

[21] Appl. No.: 896,445

[22] Filed: Jun. 10, 1992

[30] Foreign Application Priority Data

Jun. 12, 1991 [JP] Japan .................................. 3-139359

[51] Int. Cl.$^5$ .............................................. A61B 6/00
[52] U.S. Cl. ...................................... 128/653.1; 382/6; 382/22; 378/98.2
[58] Field of Search .................. 128/653.1, 653.2, 654; 382/6, 22; 358/111; 364/413.23; 378/62, 99

[56] References Cited

U.S. PATENT DOCUMENTS

| | | | |
|---|---|---|---|
| 4,263,916 | 4/1981 | Brooks et al. | 128/654 |
| 4,459,990 | 7/1984 | Barnea | 128/654 |
| 4,636,850 | 1/1987 | Stewart | 358/111 |
| 4,663,773 | 5/1987 | Haendle et al. | 378/99 |
| 4,939,760 | 7/1990 | Kawai | 378/99 |
| 4,943,987 | 7/1990 | Asahina et al. | 378/99 |
| 5,031,620 | 7/1991 | Oe | 128/653.1 |
| 5,054,045 | 10/1991 | Whiting et al. | 378/99 |
| 5,117,446 | 5/1992 | Haaker et al. | 378/99 |
| 5,161,178 | 11/1992 | Honda et al. | 378/99 |

FOREIGN PATENT DOCUMENTS

| | | | |
|---|---|---|---|
| 0362821 | 4/1990 | European Pat. Off. | 128/653.1 |
| 0366075 | 5/1990 | European Pat. Off. | |
| 3738636 | 6/1988 | Fed. Rep. of Germany. | |

OTHER PUBLICATIONS

Patent Abtracts of Japan, section C, vol. 13, No. 457, Oct. 16, 1989, & JP-A-1 178241, Jul. 14, 1989, K. Shibata, et al., "X-Ray Image Processing Apparatus".

Primary Examiner—Lee S. Cohen
Assistant Examiner—K. M. Pfaffle
Attorney, Agent, or Firm—Oblon, Spivak, McClelland, Maier & Neustadt

[57] ABSTRACT

A radiographic diagnostic apparatus for irradiating radiations to the subject for diagnosis, which comprises radiation generator section for irradiating radiations to the subject, detecting section for detecting radiations passing through the subject, and converting the detection results into image data, the image data containing first image data before catheter insertion and second image data after catheter insertion, extracting section for extracting the desired portion from the first image data, image synthesizing section for combining the portion extracted at the extracting section with either the first image data or the second image data and converting the overlapping areas in the resulting combined data into different data to form third image data, and display section for displaying the third image data obtained at the image synthesizing section.

16 Claims, 6 Drawing Sheets

APPARATUS AND METHOD FOR RADIOGRAPHIC DIAGNOSIS

BACKGROUND OF THE INVENTION

1. Field of the Invention

This invention relates to an apparatus and method for radiographic diagnosis of, for example, circulatory cases, and more particularly to an apparatus and method for radiographic diagnosis used to introduce a catheter to the target portion of the subject.

2. Description of the Related Art

In a radiographic diagnosis, particularly that of circulatory cases, operations such as PTA (blood vessel formation techniques using a catheter) are performed, the operator inserts a catheter into a blood vessel and moves the catheter along inside the blood vessel to the target portion moves it to the target portion by watching the X-ray image on the TV monitor. It is difficult, however, to decide the way in which the catheter should advance, since no blood vessel is represented on the X-ray image.

To overcome this problem, in a known method, so-called road mapping, a blood vessel contrast medium is injected at one end of the catheter, and then the catheter is advanced, while the motion of the catheter inside the blood vessel is being watched. The road mapping has two methods. One method is a method of displaying both the blood vessel image obtained by being pre injected blood vessel contrast medium thereto and an image in parallel, and watching both of them. Another method is a method of obtaining a contrast blood vessel image by subtracting an image from a blood vessel contrast image obtained by pre-injecting a blood vessel contrast medium thereto, and displaying the direction of advancing the catheter by superimposing the blood vessel contrast image on X-ray image. The latter method is called as superimpose method.

Figure 1:
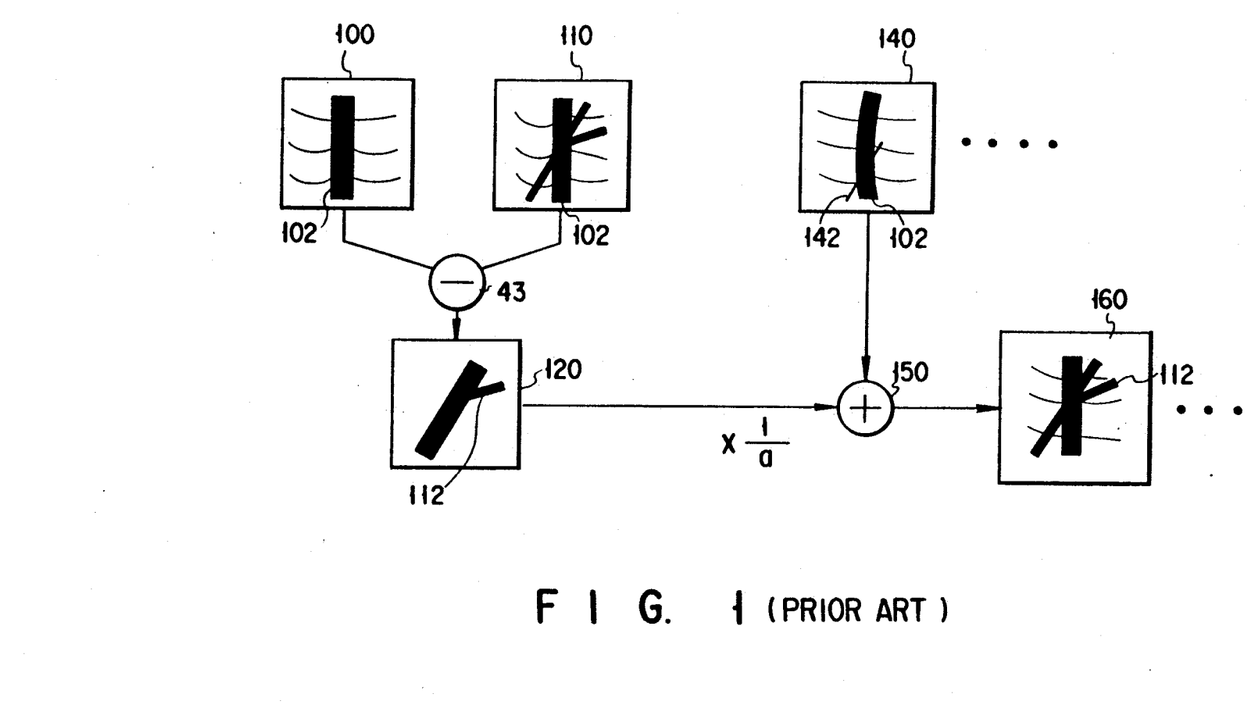
FIG. 1 is a drawing for explaining the operation of a conventional radiographic diagnostic apparatus.

An example of the superimpose method will be explained, referring to FIG. 1.

When a blood vessel contrast medium is injected through the catheter into a blood vessel, the blood vessel in which the catheter should move appears on the screen. With this operation, a contrast image 110 which contains an image 102 corresponding to a bone portion (hereinafter, referred to as a bone portion image data 102) and an image 112 corresponding to a blood vessel (hereinafter, referred to as the blood vessel image data 112) is obtained. A mask image 100 containing the bone portion image data 102 before injection of the blood vessel contrast medium is formed before the formation of the contrast image 110. After the mask image 100 is subtracted from the contrast image 110 at a subtracter 43, the background (including the bone portion image data 102 and muscle portion not shown here) is erased, creating the blood vessel image 120 consisting only of the blood vessel image 112. The blood vessel image 112 is multiplied by a given value of 1/a for brightness control.

An adder 150 adds the multiplication result, bone portion image data 120, and X-ray image 140 containing the image 142 corresponding to the catheter (hereinafter, referred to as the catheter image data 142) to superimpose each other. This addition produces a road map image 160 containing the bone portion data 102, blood vessel image data 112, and catheter image data 142.

With this road map image 160, the operator is able to easily move the catheter in the desired direction according to the blood vessel image data 112 of the map image, facilitating the maneuvering of the catheter.

Another method is to allow easy manipulation of the catheter by using a high-speed switch (not shown) to alternate between the process of displaying a blood vessel image data and the process of displaying the X-ray image containing the catheter image data to pretend to be superimposed thereof.

The superimpose method has the following problem.

Because the blood vessel image 120 is directly superimposed on the X-ray image 140, it is difficult to distinguish the catheter image 142 from the blood vessel image 120 at the overlapping portion. Since the direction of the catheter tip is very important in operations such as division of a blood vessel, a clear distinction between them is necessary. Once the blood vessel image data 112 has overlapped the catheter image data 142, it is more difficult to identify the catheter. In addition to this problem, it is less easy to watch the blood vessels and the catheter at a portion overlapping the bone image 102 and others.

Related literatures to the present invention are U.S. Pat. Nos. 4,204,225 and 4,878,115. In the former literature, a method for obtaining blood vessel image data is described, and in the latter literature, one method of superimpose method is described.

Further, another related art for observing only a blood vessel image easily by obtaining a peak hold thereof is disclosed in Japanese Unexamined Patent Application No. 1-178241. With this art, however, since a blood vessel image is displayed by only superimposing a catheter image thereon, it has a similar problem to above related art.

SUMMARY OF THE INVENTION

The object of the present invention is to provide an apparatus and method for radiographic diagnosis that allow a good grasp of the relative position of a catheter inserted into the blood vessel.

The foregoing object is accomplished by providing a radiographic diagnostic apparatus for irradiating radiations to the subject for diagnosis, comprising radiation generator section for irradiating radiations to the subject detecting section for detecting radiations passing through the subject, and converting the detection results into image data, the image data containing first image data before catheter insertion and second image data after catheter insertion, extracting section for extracting the desired portion from the first image data, image synthesizing section for combining the portion extracted at the extracting section with the second image data and converting the overlapping areas in the resulting combined data into different data to form third image data, and display section for displaying the third image data obtained at the image synthesizing section.

The foregoing object is also accomplished by providing a radiographic diagnostic apparatus for irradiating radiations to the subject for diagnosis, comprising radiation generator section for irradiating radiations to the subject, detecting section for detecting radiations passing through the subject, and converting the detection results into image data, the image data containing first image data before catheter insertion and second image data after catheter insertion, extracting section for extracting the desired portions from the first image data and second image data, image synthesizing section for combining the portion extracted at the extracting section with the first image data and converting the overlapping areas in the resulting combined data into different data to form third image data, and display section for displaying the third image data obtained at the image synthesizing section.

The first image data contains the mask image data obtained by irradiating radiations to the subject before the injection of a blood vessel contrast medium and the contrast image data obtained by irradiating radiations to the subject after the blood vessel contrast medium injection, and the extracting section contains section for obtaining blood vessel image data based on the mask image data and the contrast image data, and section for extracting the blood vessel image data corresponding to the edges of blood vessels based on the blood vessel image data.

The second image data contains the catheter image data obtained by irradiating radiations to the subject in which the catheter has been inserted, and the extracting section further includes section for obtaining catheter image data based on the catheter image data contained in the second image data and the mask image data.

Each of the blood vessel image data, blood vessel edge image data, and catheter image data is displayed in a specified brightness or in a specified color.

The foregoing object is further achieved by providing a radiographic diagnostic method for irradiating radiations to the subject for diagnosis, comprising a first step of irradiating radiations to the subject to obtain first image data before catheter insertion and second image data after catheter insertion, a second step of extracting the desired portion from the first image data, a third step of combining the portion extracted in the second step with the second image data and converting the overlapping areas in the resulting combined data into different data to form third image data, and a fourth step of displaying the third image data.

The first step contains the step of obtaining image data before the injection of a blood vessel contrast medium prior to catheter insertion and image data after the blood vessel contrast medium injection prior to catheter insertion, and the second step contains the step of obtaining the blood vessel image data on the desired portion based on the image data before and after the blood vessel contrast medium injection, and the step of obtaining the blood vessel edge image corresponding to the edges of blood vessels based o the blood vessel image data.

With an apparatus and method according to the present invention, the extracting section extracts the blood vessel edge image data corresponding only to the edges of blood vessels for special representation, so that the catheter image will not overlap the blood vessel image. Since for the area where the blood vessel edge image data overlaps the second image data, the second image data is replaced with the blood vessel edge image data of a specified brightness before display, so that the edge portions of the blood vessels are all represented at the same brightness, enabling easy identification of the blood vessel portions overlapping the third image data. Therefore, the blood vessel network is easier to see and the position of the catheter is clearer on the screen, facilitating the maneuvering of the catheter to the target blood vessel.

Since for the area where the catheter image data overlaps the blood vessel image data and/or the X-ray image data, the latter date is replaced with the former data, and the blood vessel edge image data, X-ray image data, and catheter image data are displayed in different colors or at different brightness, respectively (for example, for the area overlapping the bone portion, the blood vessels and the catheter are represented in special colors or at special brightness, the catheter having priority over the blood vessels), it is easy to move the catheter to the target blood vessel.

Additional objects and advantages of the present invention will be set forth in the description which follows, and in part will be obvious from the description, or may be learned by practice of the present invention. The objects and advantages of the present invention may be realized and obtained by section of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the present invention and, together with the general description given above and the detailed description of the preferred embodiments given below, serve to explain the principles of the present invention in which.

DETAILED DESCRIPTION OF THE PREFERRED EMBODIMENTS

Referring to the accompanying drawings, embodiments of the present invention will be explained. Although apparatuses according to this invention will be explained hereinafter, the same reasoning applies to methods according to this invention.

Figure 2:
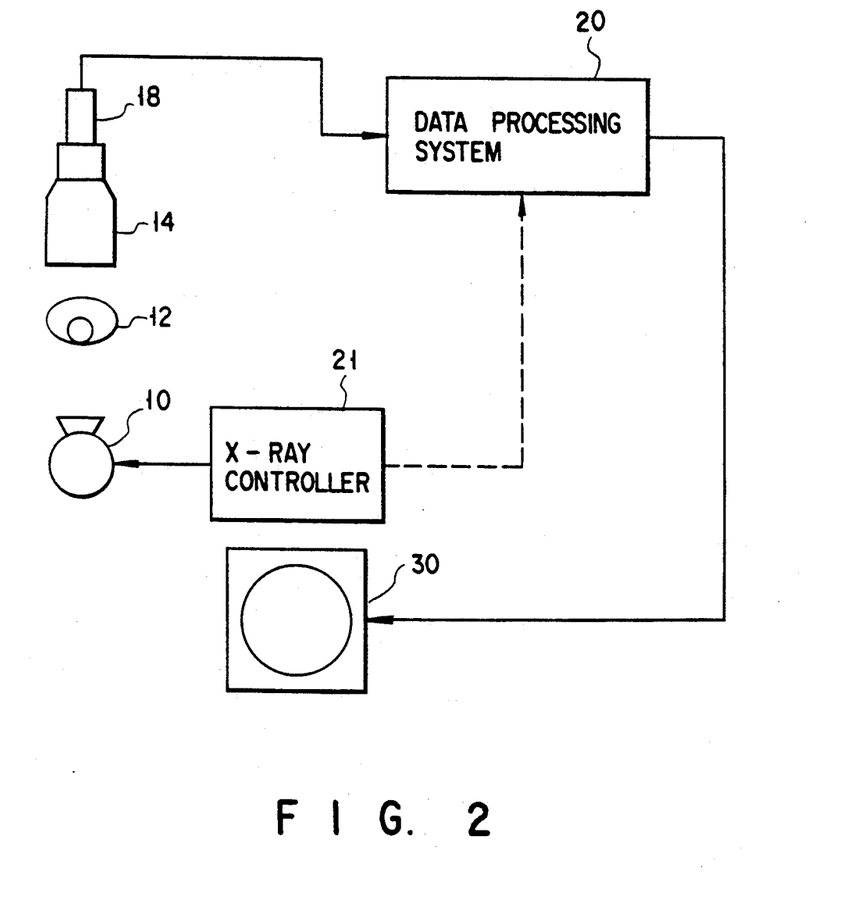
FIG. 2 is a block diagram of a radiographic diagnostic apparatus according to a first embodiment of the present invention.

FIG. 2 is a block diagram of a radiographic diagnostic apparatus according to a first embodiment of the present invention.

In FIG. 2, the radiographic diagnostic apparatus of the present invention is composed of a radiation generator 10, an X-ray controller 21, an image intensifier (hereinafter, referred to as an I. I.) 14, a TV camera 18, a data processing system 20, and a display section 30.

An X-ray tube is used as the radiation generator 10 in this embodiment. The X-ray tube 10 placed opposite the I. I. 14 irradiates X-rays to the subject 12 positioned between the tube 10 and I. I. 14.

The I. I. 14 detects and converts the X-rays passing through the subject 12 into an optical image. The optical image from I. I. 14 goes through the optical system (not shown) such as lenses and enters the TV camera 18. The TV camera converts the optical image into a TV image signal, which is supplied to the data processing system 20 explained in detail later. The TV image signal processed at the data processing system 20 is supplied as a road map image to the display section 30, which displays the road map image.

The X-ray controller 21 controls the X-ray tube 10 in terms of X-ray radiation timing as well as the data processing system 20 in terms of image processing.

The function of the data processing system 20 will be described in detail, referring to FIG. 3, a detail block diagram of this system 20.

The data processing system 20 is made up of an analog/digital converter 22 (hereinafter, referred to as the A/D converter 22), a selector switch 23, a blood vessel image generator 40, a sobel filter 46, a plane memory 47, a first multiplexer 48 (hereinafter, the first MPX 48), a second multiplexer 49 (hereinafter, the second MPX 49), and a digital/analog converter 28 (hereinafter, the D/A converter 28). The blood vessel image generator 40 is composed of an adder 41, a first to third frame memories 24a to 24c, a divider 42, a subtracter 43, and a comparator 44.

An analog signal (a TV image signal) from the TV camera 18 is converted into a digital signal at the A/D converter 22. This digital signal is supplied to either the blood vessel image generator 40 or the first MPX 48, depending on the position of the selector switch 23. Specifically, the image generator 40 receives from the selector switch 23 a signal of the mask image data (the X-ray image data before injection of blood vessel contrast medium), hereinafter referred to as the mask image data, and a signal of the contrast image data (the X-ray image data after injection of blood vessel contrast medium), hereinafter referred to as the contrast image data. The first MPX receives from the switch 23 a signal of the X-ray image data after insertion of the catheter (hereinafter, referred to as the X-ray image data).

The mask image data and contrast image data are processed at the blood vessel image generator 40 as follows.

The selector switch 23 supplies the mask image data and contrast image data to the adder 41 and comparator 44, respectively.

The mask image data at the adder 41 is supplied to the first frame memory 24a. The addition of the mask image data is continued until the mask image data has been supplied for a specified period of time, with the result that the added mask image data is stored in the first frame memory 24a. Then, the mask image data in the first frame memory 24a is divided by the number of additions of the mask image data at the divider 42 to obtain the arithmetical mean of the mask image data. This operation produces a noise-reduced mask image data, which is supplied to the subtracter 43.

The contrast image data at the comparator 44 is supplied to the second frame memory 24b, which stores this image data. Receiving the contrast image data, the comparator 44 compares the contrast image data just supplied from the A/D converter 22 with that already stored in the second frame memory 24b in terms of density on a pixel basis. Based on the comparison result, the pixels with a high density are extracted to form a contrast image data. This image data is supplied to the second frame memory 24b, which stores the data. The image data stored in the second frame memory 24b is supplied to the subtracter 43 and second MPX 49.

By repeating above operation for some frames, the contrast image data set peak hold is obtained.

The subtracter 43 subtracts the contrast image data of the second frame memory 24b from the mask image data of the divider 42, and then supplies the result to the third frame memory 24c. The third frame memory 24c stores the blood vessel image data in a manner described earlier. In the above operation, the blood vessel image generator 40 extracts the blood vessel image only.

The blood vessel image data extracted at the image generator 40 is supplied to the sobel filter 46. The sobel filter 4 detects the blood vessel edge image data corresponding only to the edges of blood vessels in the blood vessel image data supplied from the blood vessel image generator 40. This detecting method will be explained in more detail. The sobel filter 46 digital-differentiates the blood vessel image data on a pixel-group basis for binary-coding. The filter 46, which is a digital filter made up of, for example, a 3×3 template, divides the blood vessel image data into pixel groups of a specified size, using, for example, the 3×3 template. It then differentiates each pixel group in the vertical direction (for example, the Y direction) and in the horizontal direction (for example, the X direction), computes the absolute values of the differential results, and compares these absolute values with a specified threshold value for binary-coding. This operation produces the blood vessel edge image data corresponding only to the edges of blood vessels. A method of producing this blood vessel edge image data is specifically described in U.S. Pat. No. 5,056,524.

The output terminal of the sobel filter 46 is connected to the plane memory 47, which stores the blood edge image data from the filter 46. The read terminal of the plane memory 47 is connected to the first MPX 48, to which the output terminal of the A/D converter 22 is also connected.

The first MPX 48 receives the X-ray image data 140 at the time of catheter insertion, the blood edge image data 127, and a specified value "a" to control brightness. The first MPX supplies the output as follows. For 0s in the blood vessel edge image data, the first MPX supplies the X-ray image data as it is. For 1s in the area where the blood vessel edge image data overlaps the X-ray image data, the first MPX supplies a specified value "a" in place of the X-ray image data. Thus, for the 1s in the blood vessel edge data, the X-ray image data is converted into the blood edge image data with a brightness corresponding to a specified value "a." The specified value "a," which is stored in a PROM or a RAM, may be changed by the CPU or manually. The output of the first MPX is supplied to the second MPX 49.

Based on the output of the first MPX and the output of the second frame memory 24b, the second MPX supplies the road map image data to the D/A converter 28.

The D/A converter 28 converts the road map image data into an analog road map image data. The analog road map image data is supplied to the display section 30, which displays this road map image data.

The operation of the first embodiment constructed as mentioned above will be explained in detail, referring to FIGS. 2 to 4. FIG. 4 is a drawing for explaining the operation of the first embodiment.

When the X-ray switch (not shown) is turned on (at $T_0$), the X-ray controller 21 issues an X-ray radiation instruction to the X ray tube 10, which applies X-rays to the subject 12. The X-rays then pass through the subject 12 and enters the I. I. 14. The optical image converted at I. I. 14 is further converted into a TV image signal at the TV camera 18, and is supplied to the data processing system 20, which causes the A/D converter 22 to convert the optical image into digital image data.

To create the image data with no blood vessel contrast medium in the blood vessel of the subject 12, or the mask image data (the data on the mask image 100 having the bone portion data 102 in FIG. 4), the image data from the A/D converter 22 goes through the adder 41 to the first frame memory 24a, which stores this data. When the A/D converter 22 supplies the next mask image data to the adder 41, the mask image data on the preceding one frame is read from the first frame memory 24a, and supplied to the adder 41. The adder 41 adds the mask image data from the A/D converter 22 to that stored in the first frame memory 24a, and supplies the resulting mask image data to the first frame memory 24a, which stores the mask image data as accumulated mask image data. This addition is continued for a specified period of time $t_1$, preferably for nearly one second. At the time ($T_1$) when the specified time of period $t_1$ has elapsed, the add output is divided by the number of additions of the mask image data to provide the arithmetical mean of the output. This arithmetical mean decreases noises in the mask image data. The mask image data as a result of the arithmetical mean is supplied to the subtracter 43.

After the specified time elapsed $t_1$ (at $T_1$), a blood vessel contrast medium is inserted into the blood vessel to form the contrast image data (the data on the contrast image 110 containing the bone portion image data 102 and the blood vessel image data 112 in FIG. 4). The contrast image data from the A/D converter 22 is stored in the second frame memory 24b via the comparator 44. The density of the contrast image data stored in the second frame memory 24b is compared with that supplied from the A/D converter 22 at the comparator 44 on a pixel basis. Based on the comparison results, an image with pixels of high density in the contrast image data is stored in the second frame memory 24b. The above comparison is continued until the X-ray imaging has been terminated, or until a specified period of time $t_2$ has elapsed (at $T_2$) in FIG. 4.

At the time when the X-ray imaging has ceased, the mask image data and contrast image data are read from the first frame memory 24a and second frame memory 24b, respectively, and are supplied to the subtracter 43. The subtracter 43 subtracts the mask image data from the contrast image data to create a data of the blood vessel image (the data on the blood vessel image 120 having the blood vessel image data 112 in FIG. 4). The blood vessel image data 112 is supplied from the subtracter 43 to the third frame memory 24c, which stores this data.

The data of the blood vessel image stored in the third frame memory 24c is supplied to the sobel filter 46. The filter 46 divides the data of the blood vessel image into pixel groups, differentiates each pixel, and obtains the absolute value of each result. Among the absolute values thus obtained, those exceeding a specified threshold value are given, for example, a 1, and those not exceeding the threshold value are given a 0, for binary-coding. The filter 46 detects the image data corresponding to a data of the blood vessel edge (the data corresponding to the blood vessel image 125 having the blood edge image data 127 in FIG. 4), and produces the data of the binary-coded blood vessel edge image, or 1s and 0s. This data of the edge image is stored in the plane memory 47.

When X-ray imaging is started again (at $T_3$), the X-ray image data from the A/D converter 22 (the data on the X-ray image 140 containing the catheter image data 142 and bone portion image data 102 in FIG. 4) passes through the first MPX 48, second MPX 49, and D/A converter 28, for display. Specifically, as noted earlier, for the area where the contents of the plane memory 47 (the blood vessel edge image data 127) are 0s (that is, the area where only the X-ray image data exists), the first MPX 48 supplies the X ray image data as it is, whereas for the area where the contents are 1s (the overlapping area where the X-ray image data coexists with the blood vessel edge image data), a preset brightness value of "a" is supplied in place of the X ray image data.

In this way, the portions where the blood vessel image coexists with the X-ray image are given a specified brightness, and the resulting image passes through the second MPX 49 and D/A converter 28, and appears on the display section 30. To make the blood vessel edge easy to see, the value "a" is adjustable.

In the road map image thus obtained, the X-ray image is displayed in the area where no blood vessel exists, and the blood vessel edge portions are represented in a special method in the area where the blood vessels exist. Because the catheter will not overlap the blood vessels, and the blood vessels are all displayed at the same brightness, even the blood vessels overlapping the bone portions can be identified. In moving the catheter, the operator is able to easily identify the blood vessels and readily recognize the motion of the catheter.

As described above, because the operator is able to easily move the catheter to the target blood vessel, the burden of his work is reduced.

When the blood vessel edge image data is replaced with the preset value "a" at the first MPX, a more legible image can be obtained by changing the value "a" to change the density level of the blood edge image data.

Figure 5:
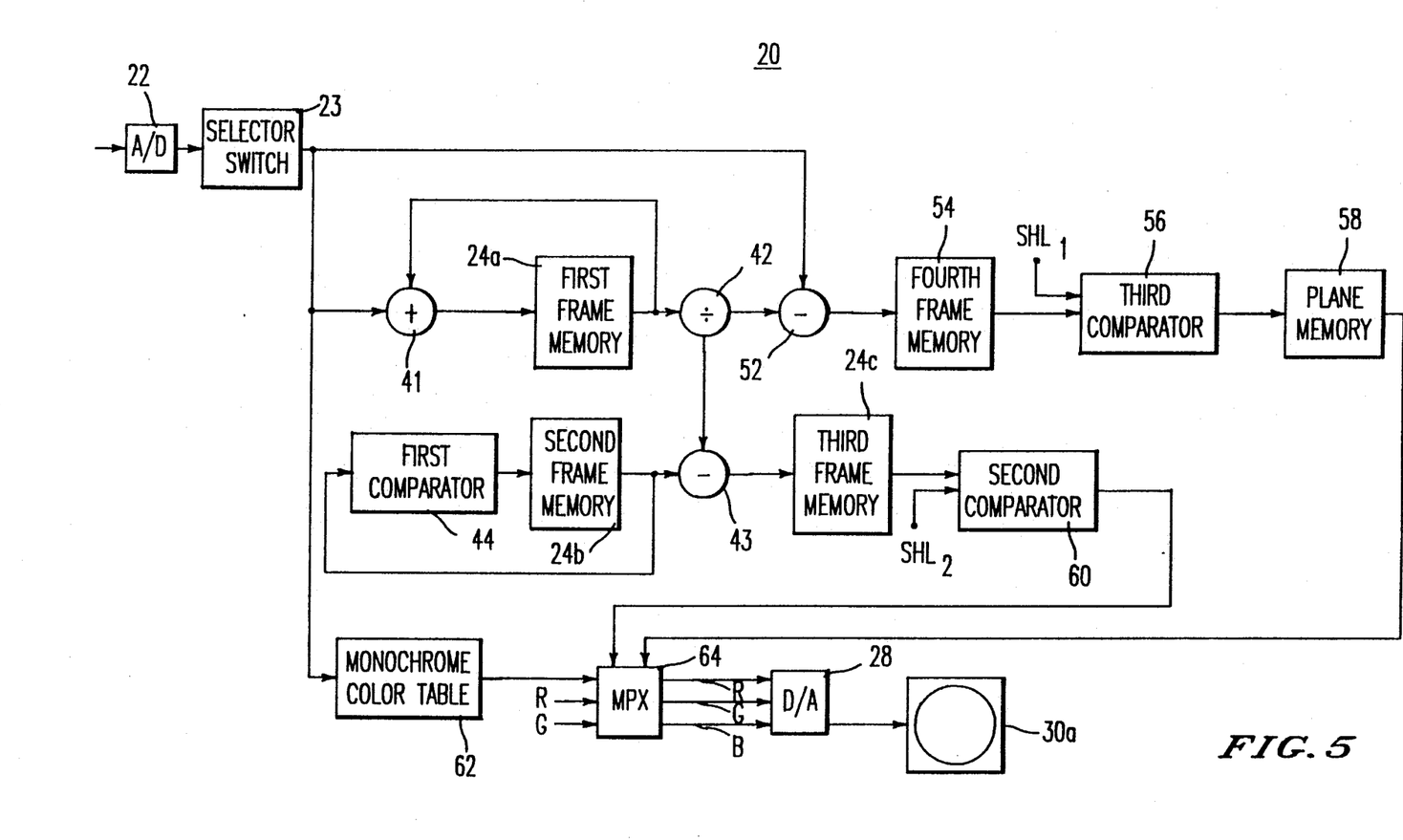
FIG. 5 is a block diagram of the data processing system, a primary portion of a second embodiment of the present invention.
Figure 6:
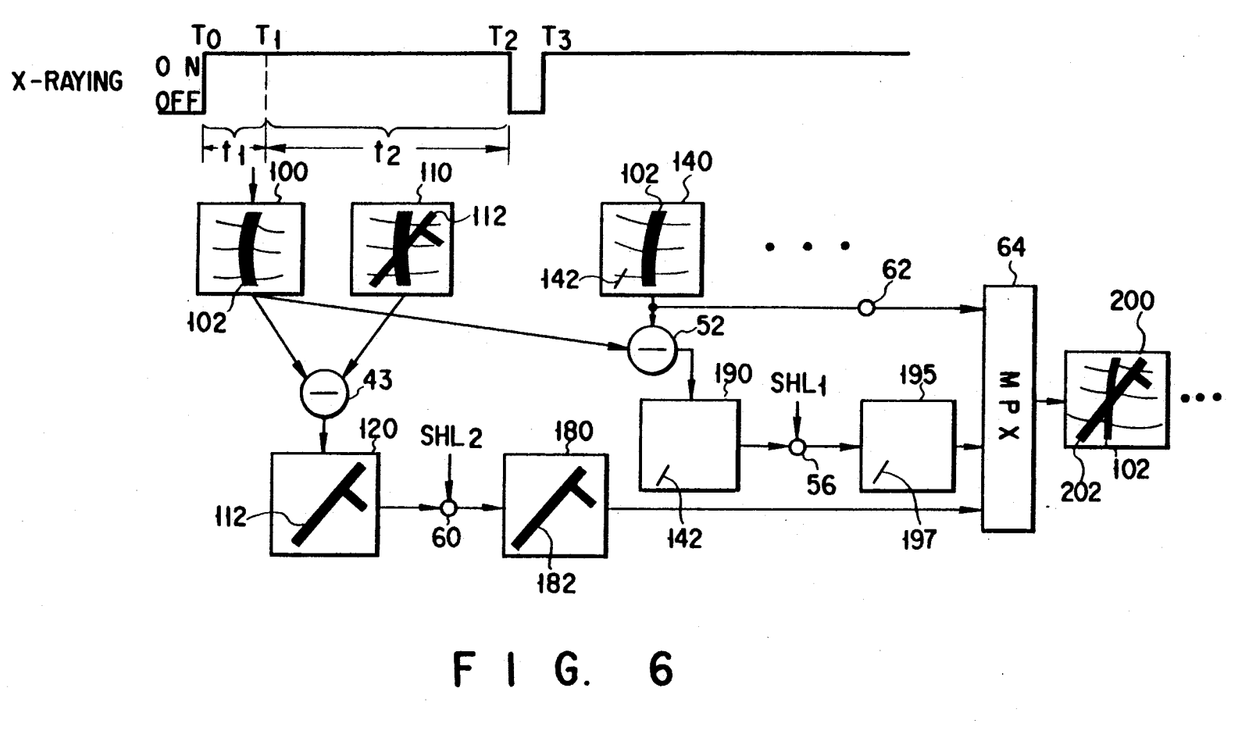
FIG. 6 is a drawing for explaining the operation of the second embodiment.

A second embodiment of the present invention will be explained, referring to FIGS. 5 and 6. The basic structure of the second embodiment is the same as that of the first embodiment, so that its explanation will be omitted. The second embodiment differs from the first embodiment in the configuration of the data processing system 20. FIG. 5 is a block diagram of the data processing system 20 of a radiographic diagnostic apparatus according to the second embodiment of the present invention. FIG. 6 is a drawing for explaining the operation of the FIG. 5 circuit. In FIGS. 5 and 6, the same parts as those in FIG. 3 are indicated by the same reference characters, and their explanation will be omitted.

The radiographic diagnostic apparatus of the second embodiment provides a special representation of the catheter image data in addition to the representation in the first embodiment, and displays the blood vessel image data, catheter image data, and X-ray image data in different colors, respectively. Here, it is assumed that the blood vessel image data is displayed in green, the catheter image data in red, and the X-ray image data in monochrome. The allocation of colors to the respective data may be made in other ways suitable for the requirements. In this embodiment, the blood vessel edge image for the blood vessel image data is not detected.

Figure 3:
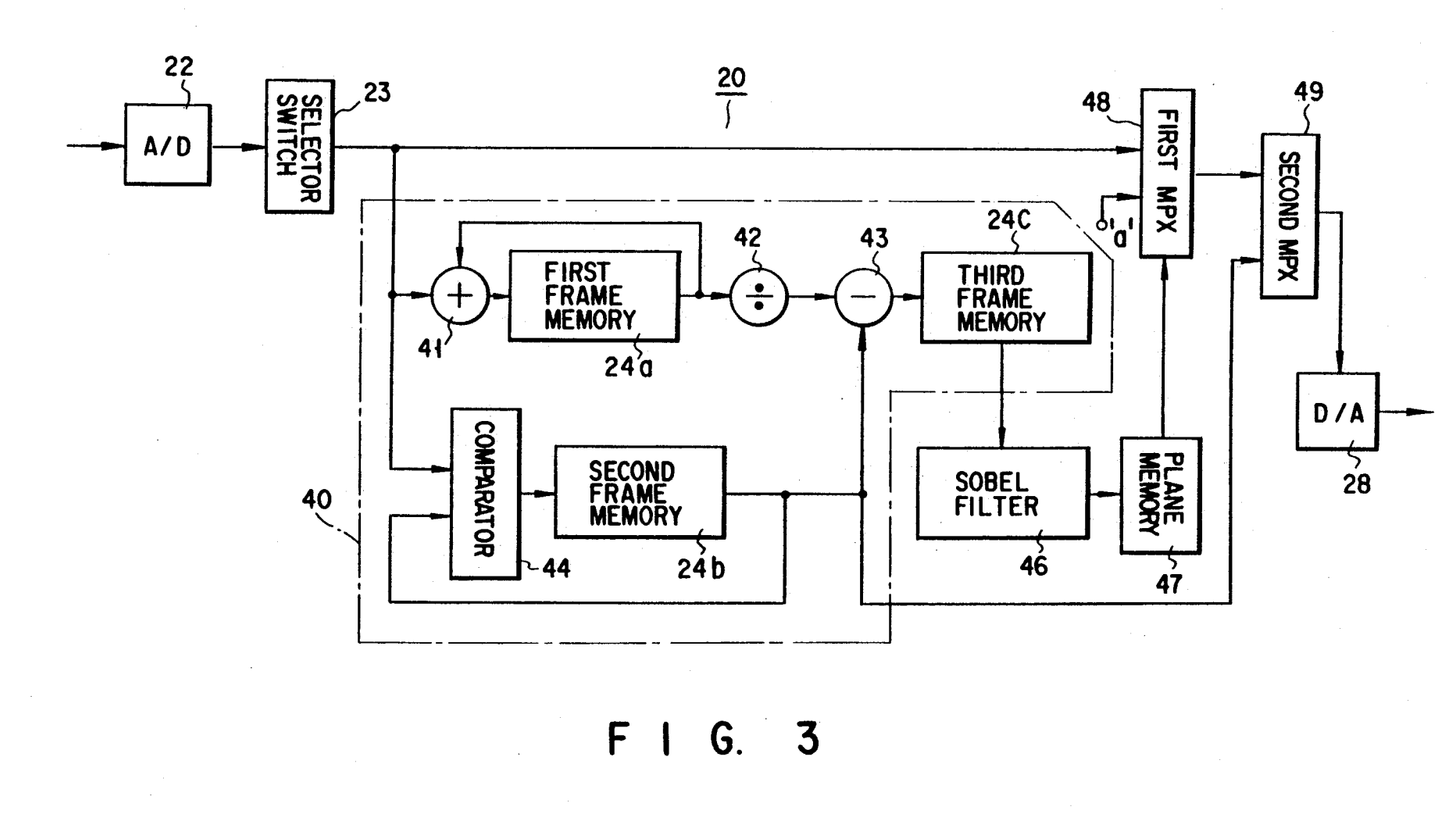
FIG. 3 is a block diagram of the data processing system, a primary portion of the first embodiment.
Figure 4:
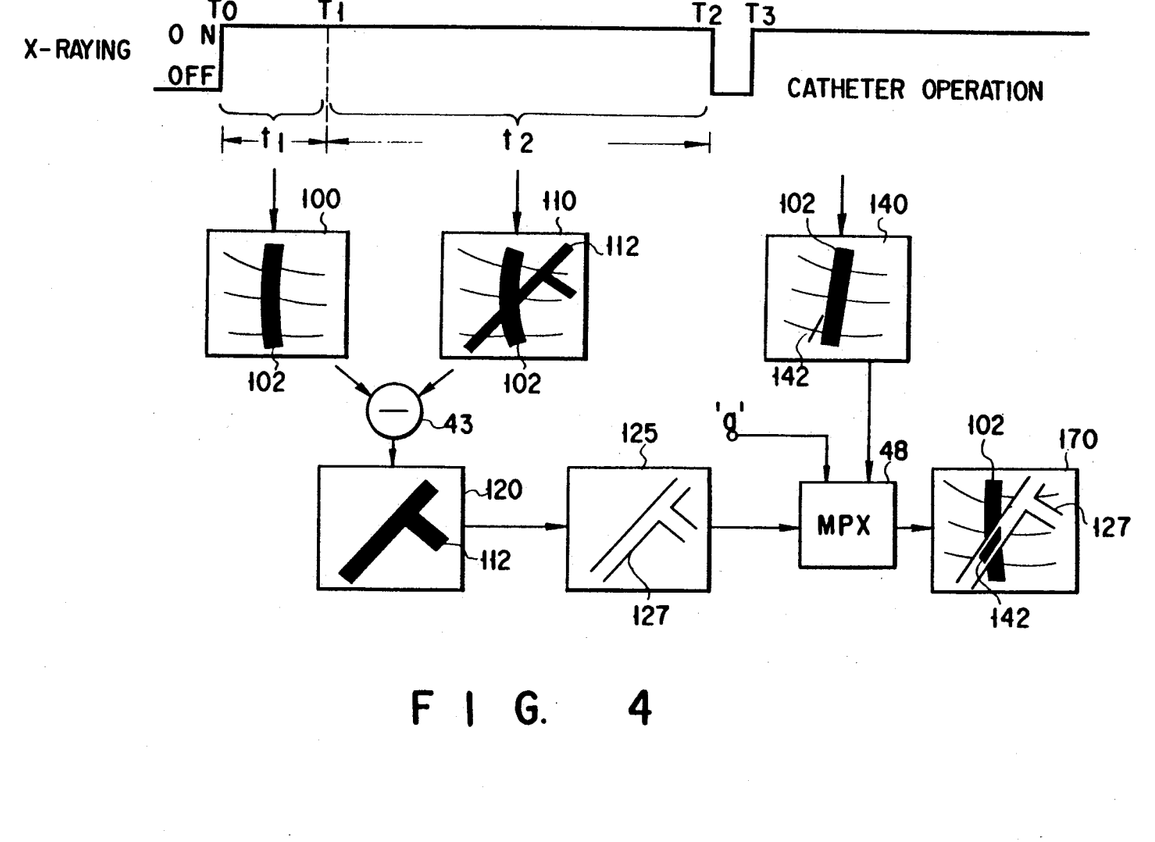
FIG. 4 is a drawing for explaining the operation of the first embodiment.

The radiographic diagnostic apparatus of FIG. 5 differs from that of the first embodiment in that a second comparator 60 is used in place of the sobel filter 46 and plane memory 47, and that a fourth frame memory 54, a third comparator 56, a plane memory 58, and a monochrome color table 62 are provided in addition to the FIG. 3 configuration.

The function of the second embodiment thus constructed will be described.

The mask image data from the A/D converter 22 is supplied to the adder 41, which supplies the result to the divider 42. The divider 42 computes the arithmetical mean and supplies the result to the first subtracter 43 and second subtracter 52. Receiving the contrast image data formed in the same manner as in the first embodiment, the first subtracter 43 subtracts the mask image data from the contrast image data, and supplies the result as the blood vessel image data to the third frame memory 24c. The third frame memory 24c stores the blood vessel image data. The blood vessel image data is read from the third frame memory, and supplied to the second comparator 60, which compares it with a specified threshold value SHL2 for binary-coding, and then supplies the resulting value to a multiplexer 64 (hereinafter, referred to as the MPX 64).

The second subtracter 52 also receives the X-ray image containing the catheter image data. The second subtracter 52 subtracts the mask image data from the X-ray image. The resulting catheter image data is supplied to the fourth frame memory 54. The catheter image data stored in the fourth frame memory 54 is supplied to the third comparator 56, which compares it with a specified threshold value SHL1 for binary-coding. This binary-coded catheter image data is supplied to the plane memory 58, which stores the data. The catheter image data from the plane memory is supplied to the MPX 64.

The X-ray data from the A/D converter 22 is supplied to the monochrome color table 62 as well as to the adder 41, first comparator 44, and second subtracter 52. The monochrome color table 62 adjusts a combination of red R, green G, and blue B in order to display the X-ray imag data from the A/D converter 22 in monochrome gradation of a luminance on the color monitor 30a.

Based on the monochrome data value for the X-ray image data from the monochrome color table 62, the blood vessel data value from the second comparator 60, and the catheter image data value from the plane memory 58, the MPX 64 switches data representation. Specifically, for example, the MPX 64 supplies to the D/A converter 28 the color for the catheter representation (green in this case) for the pixels of 1s in the catheter image data from the plane memory 58, and the color for blood vessels (red in this case) for the area where the pixels of 1s in the catheter image data from the plane memory 58 coexist with the pixels of 1 s in the blood vessel image data from the second comparator 60. For the area where the pixels of 0s in the catheter image data coexist with the pixels of 0s in the blood vessel image data, the MPX 64 supplies to the D/A converter 28 the monochrome data (containing all of R, G, and B) for the X-ray image data from the monochrome color table 62.

The display section 30a receives the digitized RGB data from the D/A converter 28, and displays a color image according to this RGB data.

The operation of the second embodiment will be explained, referring to FIGS. 5 and 6.

The mask image data 100 is formed in the same manner as in the first embodiment. The divider 42 supplies the mask image data, whose noises have been reduced by the arithmetical mean, to the first subtracter 43 and second subtracter 52.

The contrast image data 110 is formed in the same manner as in the first embodiment. The contrast image data 110 from the second frame memory 24b is supplied to the first subtracter 43. The first subtracter 43 subtracts the mask image data from the contrast image data to form the data of the blood vessel image (the data on the blood vessel image 120 having the blood vessel image data 112 in FIG. 6). This data of the blood vessel image is stored in the third frame memory 24c. The second comparator 60 compares the data of the blood vessel image from the third frame memory 24c with the threshold value SHL2. Based on the comparison result, the data of the blood vessel image is binary-coded (the data on the blood vessel image 180 having the blood vessel image data 182 in FIG. 6), and supplied to the MPX 64. The MPX 64 also receives the data on the comparison output image having the data of the binary-coded blood vessel image in FIG. 6.

The formation of catheter image data will be described. At T3, when X ray imaging is started, the second subtracter 52 subtracts the mask image data arithmetically averaged at the divider 42 from the X-ray image data (the data on the X-ray image 140 containing the bone portion image data 102 and catheter image data 142 in FIG. 6). As a result of this, the data of the catheter image (the data on the catheter image 190 containing the catheter image data 142 only in FIG. 6) is obtained. The data of the catheter image is compared with the specified threshold value SHL1 at the third comparator 56 to form the data of the binary-coded catheter image (the data on the catheter image 195 containing the catheter image data 197 in FIG. 6). This data of the binary-coded catheter image is supplied to the MPX 64.

At the same time, the X-ray image data from the A/D converter 22 is converted into monochrome data at the monochrome color table 62, and is supplied to the MPX 64. Based on the data of the binary-coded catheter image and the data of the binary-coded blood vessel image, the MPX 64 performs switching. For the area of 1s in the data of catheter image from the plane memory 58, the color for the catheter presentation (green G in this case) is supplied to the D/A converter 28. For the area where the 0sin the data of the catheter image from the plane memory 58 coexist with the 1 s in the data of the blood vessel image from the second comparator 60, the color for blood vessels (for example, red R) is supplied to the D/A converter 28. For the area where the 0s in the data of the catheter image coexist with the 0s in the data of the blood vessel image, the monochrome data on the X-ray image data from the A/D converter 22 is supplied.

On the color monitor 30a, the X-ray image is displayed together with the catheter image and blood vessel image, one on top of another, with the catheter image in green G, the blood vessel image in red R, and the X-ray image in monochrome. To prevent the colors from mixing with each other, the MPX 64 gives the highest priority to the catheter image, the second highest to the blood vessel image, and the lowest to the X ray image for display.

In the area where the catheter image exists, the catheter image is displayed in green. In the area where no catheter exists, and the blood vessel image exists, the blood vessel image is displayed in red. In the area where neither the catheter image nor the blood vessel image exist, the X ray image is represented in monochrome. The operator may change the colors for the catheter and blood vessel arbitrarily.

As noted above, the blood vessels and catheter are displayed in different colors with respect to the bone portion. Even in the areas where the blood vessels or catheter overlaps with the bone portions, the blood vessels and catheter are displayed in the same color, with the catheter having priority over blood vessels in representation. This makes it easy to identify the blood vessels and catheter, especially the catheter, facilitating the maneuvering of the catheter to the target blood vessel.

Therefore, like the first embodiment, the second embodiment alleviates the burden of the operator's work.

The present invention is not limited to the embodiments described above.

For example, in the first embodiment, each image data may be formed by radiography using higher radiation, such as DSA (digital subtraction angiography).

In the second embodiment, the mask image may be different from that used for the formation of the blood vessel image. For example, it may be formed just before the formation of the catheter image. The blood vessel image may be formed by DSA. In place of color representation, monochrome representation may be used.

While in both the first and second embodiments, X-rays are used as radiations, γ-rays may be used.

The present invention may be practiced or embodied in still other way without departing from the spirit or essential character thereof.

Additional advantages and modifications will readily occur to those skilled in the art. Therefore, the present invention in its broader aspects is not limited to the specific details, representative devices, and illustrated examples shown and described herein. Accordingly, various modifications may be made without departing from the spirit or scope of the general inventive concept as defined by the appended claims and their equivalents.

What is claimed is:

1. A radiographic diagnostic apparatus for irradiating radiations to a subject for diagnosis, comprising:
   radiation generator means for irradiating radiations to said subject;
   detecting means for detecting radiations passing through said subject, and converting a detection results into image data, said image data containing first image data before catheter insertion and second image data after said catheter insertion;
   extracting means for extracting a desired portion from said first image data;
   image synthesizing means for combining the portion extracted by said extracting means with said second image data and converting overlapping areas in the resulting combined data into different data to form third image data; and
   display means for displaying said third image data obtained by said image synthesizing means.

2. A radiographic diagnostic apparatus according to claim 1, wherein said radiation generator means is an X-ray tube.

3. A radiographic diagnostic apparatus according to claim 1, wherein said first image data contains mask image data obtained by irradiating radiations to said subject before injection of a blood vessel contrast medium and contrast image data obtained by irradiating radiations to said subject after the blood vessel contrast medium injection, and said extracting means contains means for obtaining blood vessel image data based on said mask image data and said contrast image data.

4. A radiographic diagnostic apparatus according to claim 3, wherein said extracting means contains means for detecting blood vessel edge image data corresponding to edges of blood vessels based on said blood vessel image data.

5. A radiographic diagnostic apparatus according to claim 4, wherein said blood vessel edge image data detecting means contains means for binary-coding said blood vessel image data by differentiating this data on a pixel basis and then computing absolute values of the differentiated data.

6. A radiographic diagnostic apparatus according to claim 4, wherein said blood vessel edge image data detecting means is a sobel filter.

7. A radiographic diagnostic apparatus according to claim 1, wherein said display means contains means for displaying at a specified brightness areas where preceding data has been replaced with present data by said image synthesizing means.

8. A radiographic diagnostic apparatus for irradiating radiations to a subject for diagnosis, comprising:
   radiation generator means for irradiating radiations to said subject;
   detecting means for detecting radiations passing through said subject, and converting detection results into image data, said image data containing first image data before catheter insertion and second image data after catheter insertion;
   extracting means for extracting a first desired portion from said first image data and a second desired portion from second image data;
   image synthesizing means for combining said first portion and second portion extracted by said extracting means with said first image data, and converting overlapping areas in the resulting combined data into different data to form third image data; and
   display means for displaying said third image data obtained by said image synthesizing means.

9. A radiographic diagnostic apparatus according to claim 8, wherein said detecting means comprise mask image data obtaining means for obtaining mask image data by irradiating radiations to said subject before injection of a blood vessel contrast medium and contrast image data obtaining means for obtaining contrast image data by irradiating radiations to said subject after the blood vessel contrast medium injection; and wherein said second image data contains image data of a catheter obtained by irradiating radiations to said subject in which the catheter has been inserted; and said extracting means contains means for obtaining the blood vessel image data based on said mask image data and said contrast image data, and means for obtaining the catheter image data based on said second image data and said mask image data.

10. A radiographic diagnostic apparatus according to claim 9, wherein said catheter image data obtaining means contains means for binary-coding said catheter image data.

11. A radiographic diagnostic apparatus according to claim 8, wherein said display means contains means for displaying in a specified color areas where preceding data has been replaced with present data by said image synthesizing means.

12. A radiographic diagnostic method for irradiating radiations to a subject for diagnosis, comprising:
   a first step of irradiating radiations to said subject to obtain first image data before catheter insertion and second image data after catheter insertion;
   a second step of extracting a desired portion from said first image data;
   a third step of combining said portion extracted in said second step with said second image data and converting overlapping areas in the resulting combined data into different data to form third image data; and a fourth step of displaying said third image data.

13. A radiographic diagnostic method according to claim 12, wherein said first step contains a step of obtaining image data before injection of a blood vessel contrast medium before catheter insertion and image data after the blood vessel contrast medium injection before catheter insertion, and said second step contains a step of obtaining blood vessel image data on the desired portion based on said image data before and after the blood vessel contrast medium injection.

14. A radiographic diagnostic method according to claim 13, wherein said second step contains a step of obtaining a blood vessel edge image corresponding to edges of blood vessels based o said blood vessel image data.

15. A radiographic diagnostic method for irradiating radiations to a subject for diagnosis, comprising:

a first step of irradiating radiations to said subject to obtain first image data before catheter insertion and second image data after catheter insertion;

a second step of extracting a first desired portion from said first image data and a second desired portion from said second image data;

a third step of combining said first portion and said second portion extracted in said second step with said first image data and converting overlapping areas in resulting combined data into different data to form third image data; and a fourth step of displaying said third image data.

16. A radiographic diagnostic method according to claim 15, wherein said second step contains a step of extracting blood vessel image data from said first image data and catheter image data from said second image data, and said fourth step contains a step of displaying said third image data either in different colors or at different brightness, with the catheter image data having priority over the blood vessel image data.

* * * * *